(12) United States Patent
De Caux

(10) Patent No.: US 7,514,235 B2
(45) Date of Patent: Apr. 7, 2009

(54) MEDIUM FOR IDENTIFICATION OF CANDIDA

(75) Inventor: Bryan Stevon De Caux, Basingstoke (GB)

(73) Assignee: Oxoid Limited (GB)

( * ) Notice: Subject to any disclaimer, the term of this patent is extended or adjusted under 35 U.S.C. 154(b) by 0 days.

(21) Appl. No.: 10/582,335

(22) PCT Filed: Dec. 10, 2004

(86) PCT No.: PCT/GB2004/005136

§ 371 (c)(1),
(2), (4) Date: May 10, 2007

(87) PCT Pub. No.: WO2005/059169

PCT Pub. Date: Jun. 30, 2005

(65) Prior Publication Data

US 2007/0218521 A1    Sep. 20, 2007

(30) Foreign Application Priority Data

Dec. 13, 2003  (GB) ................... 0328912.1

(51) Int. Cl.
*C12Q 1/04* (2006.01)
*C12N 1/00* (2006.01)
(52) U.S. Cl. .................... 435/34; 435/255.4; 435/255.7
(58) Field of Classification Search ........................ None
See application file for complete search history.

(56) References Cited

U.S. PATENT DOCUMENTS 5,534,415 A   7/1996   Orenga et al.
5,716,799 A   2/1998   Rambach et al.

OTHER PUBLICATIONS

Sakai et al. ((1996) Biochem Biophys Acta 1308: 81-87.*
Tani et al. ((1990) Appl. Microbiol. Biotechnol 34:5-9.*
Pfaller et al. (1996), Application of CHROMagar *Candida* for Rapid Screening of Clinical Specimens for *Candida albicans, Candida tropicalis, Candida krusei,* and *Candida (Torulopsis) glabrata, Journal of Clinical Microbiology*, vol. 34, No. 1, pp. 58-61.
Willinger et al., (2001), Performance of *Candida* ID, a new Chromogneic Medium for Presumptive Identification of *Candida* Species, in Comparison to CHROMagar *Candida, Journal of Clinical Microbiology*, vol. 39, No. 10, pp. 3793-3795.
International Search Report mailed Mar. 7, 2005 for International Application No. PCT/GB2004/005136.

* cited by examiner

*Primary Examiner*—Lisa J Hobbs
(74) *Attorney, Agent, or Firm*—Rader, Fishman & Grauer PLLC

(57) ABSTRACT

Disclosed is a medium for the detection and/or identification of a *Candida* yeast, the medium comprising: a chromogen; carbohydrate in the range 1-5 gms/liter; and an alcohol; the medium being such that growth of the *Candida* yeast under appropriate conditions results in hydrolysis of the chromogen to generate a chromophore of a derived color which is a different color from that generated by hydrolysis of the chromogen in a standard medium.

16 Claims, 1 Drawing Sheet

MEDIUM FOR IDENTIFICATION OF CANDIDA

FIELD OF THE INVENTION

The present invention relates to a medium for the growth and/or identification of micro-organisms, and to a method of identification of a micro-organism using the medium.

BACKGROUND OF THE INVENTION

The detection and identification of micro-organisms is very important in several fields, such as diagnosis of infectious disease, tracing sources of outbreaks of disease or contamination, detecting and tracing the spread of antibiotic resistance etc.

Many methods of detecting and identifying micro-organisms have been derived in recent years, employing sophisticated techniques, such as PCR and the like. These are frequently rapid and extremely sensitive. However, there is still a need for more traditional methods involving the culturing of organisms on media (especially solid media). These traditional methods have the great advantage that they result in isolation of organisms of interest in viable form, which can then be sub-cultured into other media and/or further analysed.

It is well-known to include in such media compounds which may allow or promote the growth of certain micro-organisms whilst preventing or inhibiting the growth of other micro-organisms. Such media are said to be "selective". For example, certain antibiotics may be incorporated into media to allow the growth of micro-organisms which are sufficiently resistant to the antibiotic(s) employed.

It is also well known to include in media (which may or may not be selective) substances which allow different (possibly closely-related) micro-organisms to be distinguished. Such media may be described as "differential media".

One such differential medium is disclosed in U.S. Pat. No. 5,716,799 (Rambach). The medium disclosed in that document comprises: at least one chromogen which is a substrate for an enzyme of the particular micro-organism to be identified, together with a carbohydrate at high concentration (10-30 gms/liter). The medium is such that, in the presence of the micro-organism of interest, the chromogen is hydrolysed to release a chromophore with a "derived colour" which is different to the basic colour of the chromophore in a "standard" medium. (A "standard" medium is defined in that document as being "any ordinary identification medium in which the carbohydrate has a simple function of a carbon source, at very low or even zero concentrations".)

Thus, the teaching of U.S. Pat. No. 5,716,799 is that it is an essential feature of the invention described therein that the medium contains a high concentration (i.e. 10-30 gms/liter) of carbohydrate. A medium in accordance with U.S. Pat. No. 5,716,799 is commercially available from Becton Dickinson, USA and is known as CHROMagar™ Candida.

The medium disclosed in U.S. Pat. No. 5,716,799 is useful in discriminating between different yeasts of the genus *Candida*. In particular, there is a clinical significance attached to the ability of distinguishing between *Candida albicans* and other species of *Candida*. *C. albicans* is a frequent human pathogen, but other *Candida* species may also be present. Also, different *Candida* species have different susceptibilities to antifungal therapy, so it is important to determine if an organism of the genus *Candida* is *C. albicans* or some other *Candia* species.

U.S. Pat. No. 5,534,415 (Orenga) also discloses an identification medium, specifically a medium for the selective detection of *C. albicans*. The medium disclosed therein comprises a chromogenic or fluorogenic substrate capable of being hydrolysed by a hexosaminidase enzyme "associated" with *C. albicans*, and at least one hexosamine-containing "activator" compound (different to the substrate) present at about 1 gm/liter. A medium in accordance with U.S. Pat. No. 5,534,415 is commercially available (from bioMérieux, France) and is known as *Candida* ID. Hydrolysis of the chromogen in the medium does not give rise to a derived colour (that is, the chromophore has the same colour in the *Candida* ID medium as it does in a standard medium).

Willinger et al (2001 J. Clin. Microbiol. 39, 3793-3795) conducted a trial to compare the performance of CHROMagar™ *Candida* and *Candida* ID, using nearly 600 clinical specimens. On CHROMagar™ *Candida* plates, colonies of *C. albicans* were green, whilst other colonies of other *Candida* species were pink, violet or white. On *Candida* ID plates, *C. albicans* colonies appeared blue, whilst other *Candida* species were pink or white.

Willinger et al found that, for about 50% of specimens, identification of *C. albicans* was more rapid on *Candida* ID plates than on CHROMagar™ *Candida* plates, the blue colour on *Candida* ID plates typically appearing after 24 hours' incubation at 35° C., whilst the green colour of *C. albicans* colonies on CHROMagar™ *Candida* plates often was not apparent until incubation for about 48 hours. This was expected, in that the *Candida* ID medium contains a hexosamine activator which, it is presumed, accelerates induction of the hexosaminidase enzyme which acts on the chromogen, whilst CHROMagar™ *Candida* medium does not contain any such activator. However, they also found that "*Candida* ID is not as good as CHROMagar™ *Candida* in detecting polyfungal specimens".

In addition, CHROMagar™ *Candida* is superior to *Candida* ID in terms of its ability to allow different *Candida* species to be distinguished. *Candida* ID medium is very effective at distinguising between *C. albicans* and other species of *Candida* but cannot, for example, allow for efficient differentiation between *C. tropicalis* and other non-*albicans* species. CHROMagar™ *Candida*, in contrast, allows for the identification of a number of *Candida* species, including *C. tropicalis*, since various species give different "derived" colour changes on the medium. *Candida* ID medium does not give a "derived" colour chromophore which is different to that obtained with a basic medium.

The present invention is concerned with media for micro-organisms, especially differential media and, in particular, a medium which allows for discrimination between different species of *Candida*.

The content of all publications mentioned in this specification is specifically incorporated herein by reference.

SUMMARY OF THE INVENTION

In a first aspect the invention provides a medium for the detection and/or identification of a *Candida* yeast, especially *C. albicans*, the medium comprising: a chromogen; carbohydrate in the range 1-5 gms/liter; and an alcohol; the medium being such that growth of the *Candida* yeast under appropriate conditions results in hydrolysis of the chromogen to generate a chromophore of a derived colour which is a different colour from that generated by hydrolysis of the chomogen in a standard medium.

For present purposes, a "derived colour" means any colour (generated by hydrolysis of the chromogen in a medium in accordance with the invention) whose dominant wavelength differs from the dominant wavelength of the chromophore generated by hydrolysis of the chromogen in a "standard medium". Again for the purposes of the present specification, a "standard medium" may be defined as a medium essentially lacking an alcohol but otherwise in accordance with the invention. In particular, the derived colour is preferably produced by hydrolysis of the chromogen as a result of the growth and/or presence of C. albicans in/on the medium, such that the presence of C. albicans may be determined by the appearance in the medium of the chromophore exhibiting derived colour.

The dominant wavelength of the chromophore may be determined by reference to daylight, as defined by the CIE, using any conventional technique for measuring the colour of an object (e.g. with a spectrocolourimeter).

In most instances the colour difference between the derived colour of the chromophore and the normal colour of the chromophore will be readily apparent to the naked eye of a human observer.

The medium is especially useful in the detection and/or identification of C. albicans and C. tropicalis, and in particular in allowing differentiation between C. albicans and other Candida species. The medium is preferably a solid medium. Conveniently the medium may be solidified by the inclusion of agar at an appropriate concentration (e.g. 10-20 gms/liter).

In a second aspect the invention provides a method of detecting and/or identifying a Candida yeast in a sample (especially wherein the sample may contain other microorganisms, such as yeasts and, in particular, a plurality of other yeasts of the genus Candida). The method involves use of the medium of the first aspect of the invention.

More specifically, the method of the invention comprises the steps of: contacting the sample with the medium of the first aspect of the invention defined above, under appropriate conditions, to allow growth of the Candida yeast; and detecting the presence of a chromphore having a colour indicative of the presence of the Candida yeast. The method of the invention is especially useful for, but not necessarily limited to, distinguishing C. albicans from other Candida species.

The inventor has surprisingly found that, contrary to the teaching of U.S. Pat. No. 5,716,799, it is possible to discriminate between Candida species using a medium which does not contain a high concentration of carbohydrate.

DETAILED DESCRIPTION OF THE INVENTION

Carbohydrate

Figure 1:
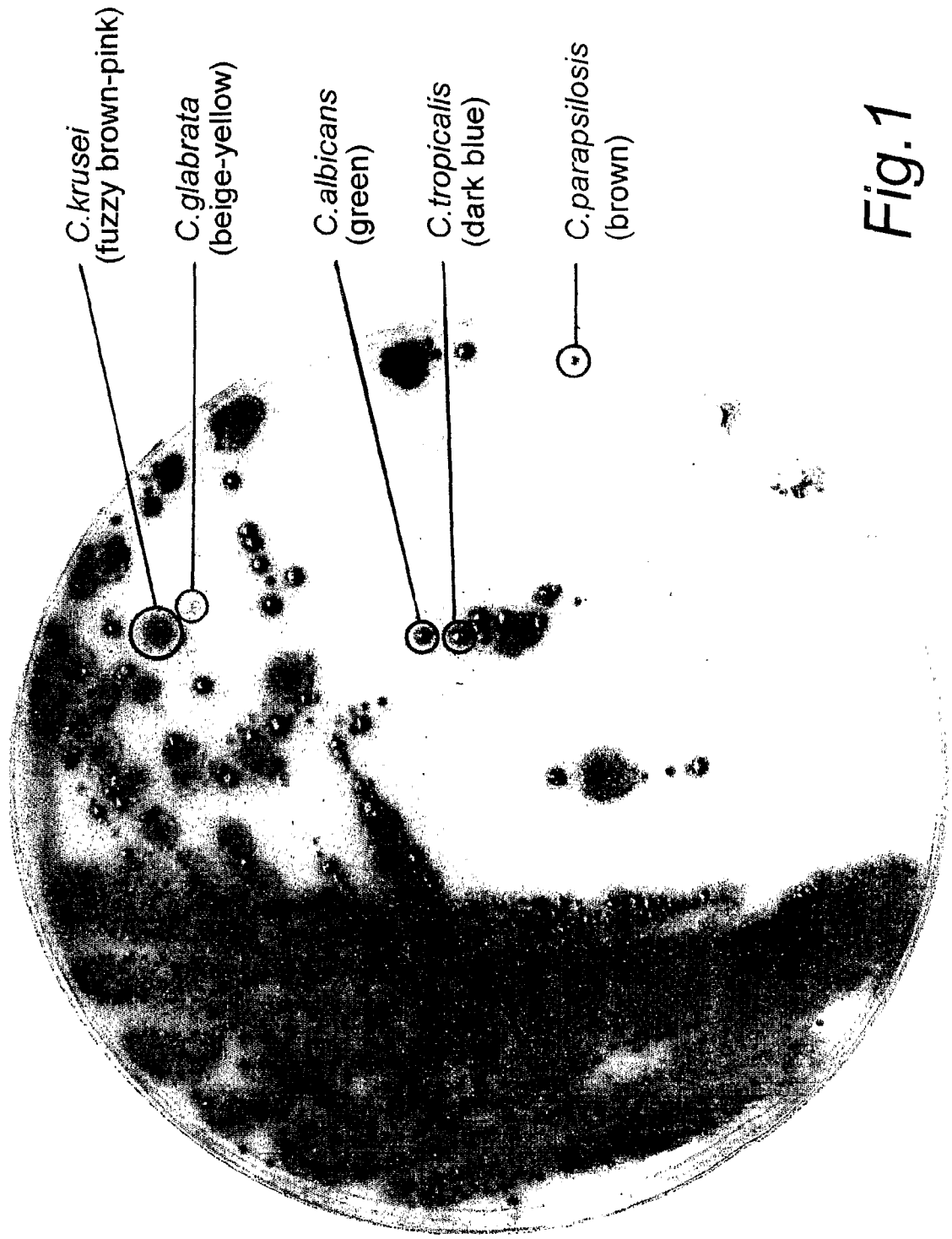
FIG. 1. Photograph of a plate showing the growth of the inoculum and separate colonies.

Carbohydrate used in the medium of the present invention may, in principle, be any carbohydrates which are capable of being used as a carbon source by Candida. The carbohydrate content preferably comprises at least some sugars, especially mono- or disaccharides. In particular pentose or hexose monosaccharides are especially convenient. The most preferred sugar is glucose. The carbohydrate content may additionally or alternatively comprise more complex saccharides with a higher degree of polymerisation. A convenient source of carbohydrate is malt extract, which is readily available commercially. In one embodiment the medium comprises both glucose and malt extract in an amount such that the total concentration of carbohydrate (glucose plus malt extract and those carbohydrates (if any) present in the peptones) in the medium is in the range 1-5 gms/liter.

The carbohydrate is preferably incorporated into the medium at a concentration in the range 2-4 gms/liter.

Alcohol

The alcohol is preferably present in the medium at a concentration which does not exert a significant inhibitory effect on the growth of Candida yeasts. A suitable concentration for most alcohols is in the range 1-10 mls/liter, preferably 2-8, more preferably 5-7 mls/liter.

In particular, the alcohol employed in the medium and method of the invention is an alcohol which is not a carbohydrate. The person skilled in the art understands carbohydrates to be "polyhydroxy aldehydes i.e. H—$[CHOH]_n$—CHO or polyhydroxy ketones i.e. H—$[CHOH]_n$—CO—$[CHOH]_m$—H with three or more carbon atoms" or "substances derived from monosaccharides by reduction of the carbonyl group by oxidation of one or more terminal groups to carboxylic acids, or by replacement of one or more hydroxyl groups by a hydrogen atom, an amino group, a thiol group or similar heteroaromatic groups" (International Union of Pure & Applied Chemistry [IUPAC] definition of Carbohydrates).

Thus, for example, in the present invention the alcohol may be a mono-alcohol, or a di-alcohol without an aldehyde or keto group.

The alcohol may be an aromatic, alicyclic, or aliphatic (straight chain or branched) compound, although saturated aliphatic compounds are generally preferred.

More especially the alcohol preferably comprises between 1 and 5 carbon atoms, preferably 2-4 carbon atoms. Ethanol (99.7-100% v/v) is presently the preferred alcohol, although industrial methylated spirits ("IMS"), comprising a mixture of about 85% ethanol and about 10% methanol, is also suitable and is commercially available at a cost lower than pure ethanol.

Chromogen

The medium of the invention comprises at least one chromogen, although two or more chromogens may be used if desired. The chomogen is a compound which, in the presence of species specific enzymes and in suitable conditions, is hydrolysed to release a chromophore which is of a colour discernibly different to the colour of the chromophore generated by growth of the same yeast in a standard medium containing the same chromogen.

The chromogen preferably comprises a hexosaminide, most preferably a glucosaminide, and typically conforms to the general formula X-GluNAc (wherein Glu is glucose, NAc is an N-acetyl group and X is a chromophore). Many suitable chromogens are known to those skilled in the art. A preferred chromogen is 5-bromo-4-chloro-3-indolyl N-acetyl β-D-glucosaminide. Other chromogens which may additionally or alternatively be used include 5-bromo-6-chloro-3-indolyl N-acetyl β-D-glucosaminide, X-Gal NAc (wherein Gal is galactose, NAc is an N-acetyl group and X is a chromophore), 5-bromo-6-chloro-3-indolyl phosphate p toluidine salt, 5-bromo-4-chloro-3-indolyl phosphate p toluidine salt and 6-chloro-3-indoxylphosphate.

Other Components

The medium will generally comprise additional components which are present in a typical conventional yeast medium, such as agar, yeast extract, sodium chloride and one or more antibiotics (e.g. chloramphenicol) to suppress bacterial growth.

In a preferred embodiment, the medium may also contain one or more of the following: malic acid (at about 0.1 gms/liter); peptones (at about 2.5 gms/liter); and a buffer (e.g. $KH_2PO_4$, at about 2.0 gms/liter).

The method of the invention involves contacting a sample to be tested with a medium in accordance with the first aspect of the invention, and incubating the medium under conditions to allow growth of Candida organisms, if present. Typically the sample will comprise a suspension of yeast cells and other material and may be, for example, a clinical sample obtained from a patient. The sample will normally be spread over the surface of a solid medium, contained within a Petri dish or other suitable container. The medium to which the sample has been applied must then be incubated at an appropriate temperature and for sufficient length of time to allow growth of any yeast cells in the sample to a sufficient extent to cause hydrolysis of the chromogen. Typically the temperature of incubation is in the range 10-37° C., more preferably 20-35° C., and most preferably 25-30° C. The length of incubation depends, at least in part, on the incubation temperature, but for an incubation temperature in the range 25-30° C. an incubation of 24-48 hours duration is usually adequate. If a result is not apparent after 24 hours, the plates can simply be returned to the incubator and re-inspected at say, 36 or 48 hours.

Typically, for a medium in accordance with preferred embodiments of the invention, the colour of the chromophore will be green or green/blue in the presence of C. albicans, purple or blue in the presence of C. tropicalis and pink in the presence of C. krusei, where the chromogen is 5-bromo-4-chloro-3-indoxyl N-acetyl β-D-glucosaminide. Green and green/blue constitute derived colours: the normal colour of the chromophore in a standard medium is purple or blue. These colour differences are readily apparent to the naked eye. If desired, control cultures of known C. albicans and/or known C. tropicalis strains, for example, can also be set up to give a comparison with the test culture.

For the avoidance of doubt, it is expressly stated that any feature of the invention described herein as "preferred", "preferable", "advantageous", "desirable" or the like may be employed in the invention in isolation or in combination with any other feature or features so described, insofar as the context permits.

The invention will now be further described by way of illustrative example.

EXAMPLES

Example 1

A basic yeast medium formulation was prepared, according to the Table below:

TABLE 1

Basic yeast medium

| Ingredient | gm/l |
|---|---|
| Agar | 15 |
| Yeast extract | 2 |
| Peptone | 2.5 |
| Malic acid | 0.1 |
| Glucose | 0.5 |
| Malt extract | 1.5 |
| Sodium chloride | 2.5 |
| 5-bromo-4-chloro-3-indoxyl N-acetyl β-D glucosaminide | 0.1 |
| 5-bromo-6-chloro-3-indoxyl phosphate p toluidine salt | 0.08 |
| Chloramphenicol | 0.1 |
| (Total | 24.38 gm/l) |

Various test media (in accordance with the invention) or comparative media (outside the scope of the invention) were prepared by supplementing the basic formulation as follows:

TABLE 2

| Example | Basic formulation supplemented with: | Notes | |
|---|---|---|---|
| A | 6 ml IMS | 1 | |
| B | 6 ml ethanol | 2 | |
| C | 6 ml butanol | | |
| D | CHROMagar ™ Candida | 3 | 6 |
| E | 4 ml methanol | 4 | |
| F | 6 ml propan-2-ol | | |
| G | 2 gm/l sodium succinate | | 6 |
| H | 2 gm/l sodium citrate | | 6 |
| I | 6 ml/l ethyl acetate | 5 | 6 |
| J | 6 ml/l ethanol | 5 | |
| K | 6 ml/l H$_2$O | 5 | 6 |

Notes
1. IMS is approximately 85% ethanol, 10% methanol.
2. Ethanol was at least 99.7% ethanol v/v.
3. 47.7 gm/l CHROMagar ™ Candida, for comparison.
4. (6 ml/l methanol was found to inhibit growth of many Candida strains).
5. Media I, J and K contained carbohydrate at 4 gm/l, twice the concentration of carbohydrate in media A-H. This was obtained simply by doubling the amount of glucose and malt extract to 1 gm/l and 3 gm/l respectively.
6. Comparative example, outside the scope of the invention.

The final pH of formulations A-C and E-H was adjusted to 6.0 with NaOH or HCl as appropriate. The commercially available CHROMagar™ Candida medium (formulation 'D') was found to have a pH of 6.03. The pH of formulations I-K was found to be about 5.8 and was not adjusted.

The various media formulations were tested for their ability to give rise to a derived colour change with a number of Candida yeast strains, which were either available within the Oxoid yeast culture collection (OYC) or were clinical isolates. The table below shows the yeast strains tested (in this or subsequent example):

TABLE 3

| | Yeast Strains | | |
|---|---|---|---|
| Strain | NCPF equivalent | ATCC equivalent | Notes |
| OYC247 (C. albicans) | 3153 | | |
| OYC205 (C. albicans) | 3179 | 10231 | NCYC1363 |
| OYC263 (C. albicans) | | 2091 | NCYC854 |
| OYC238 (C. albicans) | | 18804 | NCYC597 |
| OYC249 (C. glabrata) | 3240 | | |
| OYC225 (C. kefyr) | | 8555 | |
| OYC223 (C. tropicalis) | | 750 | |
| NCYC4 (C. tropicalis) | | | NCYC4 |
| OYC222 (C. krusei) | | 6258 | |

NCPF—National Collection of Pathogenic Fungi, PHLS Mycological Reference Laboratory, 61 Colindale Avenue, London NW9 5HT, United Kingdom.
ATCC—American Type Culture Collection, Manassas, Va 20108, USA.
NCYC—National Collection of Yeast Cultures, Institute of Food Research, Norwich Research Park, Colney, Norwich NR4 7UA, United Kingdom.
All strains without an NCPF or ATCC equivalent are available on request from Oxoid Limited.

The various strains were grown on Sabouraud Dextrose agar plates. Growth from the plates was then used to prepare suspensions in saline solution, each suspension being adjusted to a turbidity of 1 McFarland Unit. Pure cultures of these suspensions were then streaked onto the various agar formulations and incubated at 30° C. for up to 48 hours. The results are shown below:

TABLE 3A

| Formu-lation | OYC247 (C. albicans) | OYC263 (C. albicans) | NCYC4 (C. tropicalis) |
|---|---|---|---|
| A | Green | Dark green | Purple-blue |
| B | Green | Dark green | Purple |
| C | Green-blue | Blue-green | Blue-green |
| D | Green-yellow | Green-grey | Purple-blue |
| E | DarkBlue/Blue-green | Blue-violet/Green | Purple |
| F | Dark Blue/Blue-green | Violet/Blue-green | Purple |
| G | Dark blue/Blue-green | Blue-green | Pink-purple |
| H | Dark blue | Violet/Blue-green | Pink-purple |
| I | Blue-green | Blue-violet/Blue-green | Purple/Blue-grey |
| J | Green | Green | Purple |
| K | Blue/Blue-light green | Blue-light green | Purple/Blue-grey |

| Formu-lation | OYC223 (C. tropicalis) | OYC222 (C. krusei) | OYC 249 (C. glabrata) | OYC 225 (C. Kefyr) |
|---|---|---|---|---|
| A | Blue-purple-grey | Pink-purple | Not done | Not done |
| B | Blue-purple-grey | Pink-purple | " | " |
| C | Blue-green | Pink-purple | " | " |
| D | Blue-purple | Pink-Lt purple | " | " |
| E | Dark blue/Dark purple | Pink-purple | " | " |
| F | Purple-blue-grey | Pink-purple | " | " |
| G | Purple-Lt grey | Pink-purple | " | " |
| H | Purple-Lt grey | Pink-purple | " | " |
| I | Blue-violet | Pink | " | " |
| J | Blue-grey | Pink | Light pink/beige | Dark pink |
| K | Blue-purple | Pink | Beige | Pink |

From the results it is clear that only the agar plates comprising the combination of alcohols and low carbohydrate concentration were able to give a derived colour change for *C. albicans*. Other carbon sources, such as succinate (formulation G), citrate (formulation H) or ethyl acetate (formulation I) were ineffective.

The most effective formulation in accordance with the invention, in terms of giving a clear derived colour change for *C. albicans*, was formulation J, comprising 6 mls/l ethanol and 4 gms/l carbohydrate. Accordingly, ethanol (and, to a lesser extent, IMS) is the preferred alcohol for use in media and methods in accordance with the present invention. Formulations A and B also gave acceptable results.

Example 2

A further experiment was performed to compare a medium in accordance with the present invention (essentially corresponding to formulation J as described in Example 1), with the commercially available media Candida ID and CHROMagar™ Candida.

Pure cultures of various *C. albicans* strains were grown on Oxoid Sabouraud Dextrose agar plates for 48 hours, and these used to prepare cell suspensions in saline solution having a McFarland turbidity equivalent to standard 1. The suspensions were then streaked onto test plates using the diminishing streak technique, and incubated at 30° C. for 24 hours.

After 24 hours, colour was generally apparent only on the most heavily inoculated parts of the plates (first and second zones of inoculation). Single colonies, on all plates, generally lacked colour. The results are shown below.

TABLE 4

| C. albicans Strain | Candida ID (BioMerieux Lot 776691301) | CHROMagar Candida (BD) Lot 402-c | Invention Medium |
|---|---|---|---|
| PAD 32121 | Blue | Green | Green |
| PAD 32365 | Blue | Green | Green |
| OYC 238* | White | White | Green |
| PAD 32605 | Pale blue | Green | Green |
| PAD 31989 | Blue | Green | Green |
| PAD 31986 | Blue | Green | Green |
| PAD 32755 | Blue | White | Green |
| PAD 32770 | Blue | Green | Green |
| PAD 32651 | Colourless (ppt) | Colourless (ppt) | Colourless (ppt) |
| PAD 32433 | Pale blue | Green | Green |
| PAD 32617 | Pale Blue | Green | Green |
| OYC 205* | Blue | Green | Green |
| PAD 32777 | Blue | Green | Green |
| PAD 32611 | Blue | Green | Green |
| PAD 222973 | Blue | Green | Green |
| PAD 31987 | Blue | Green | Green |
| PAD U32184 | Blue | Green | Green |
| OYC 263* | Blue | White | Green |
| PAD 31984 | Blue | Green | Green |
| PAD 32289 | Blue | Green | Green |
| Total positive (24 h) | 18/20 | 16/20 | 19/20 |

PAD = Pure clinical isolates from St. Mary's Hospital, Paddington, London.
OYC = Oxoid Culture Collection
*Candida* ID - *C. albicans* should give a blue colour (i.e. no derived colour change)
*see Table 3
All the strains used in this experiment are available from Oxoid upon request.

The results show that, whilst all three media performed well, after 24 hours' incubation the medium in accordance with the invention returned more positive results than the CHROMagar™ *Candida* medium. The medium of the invention was also comparable, or possibly even slightly superior, to the *Candida* ID medium in terms of positive results obtained after 24 hours. This was extremely surprising and unexpected (in relation to Willinger et al, who found 335/384 *C. albicans* grown on *Candida* ID compared to 167/370 grown on CHROMagar™ *Candida* that were correctly identified at 24 hours), given that the *Candida* ID medium comprises a hexosaminide activator to accelerate induction of the relevant hexosaminidase.

After 48 hours incubation, all media gave positive results with all 20 strains tested, and most individual colonies were coloured. However, growth of PAD 32651 on the *Candida* ID medium was poor, and many individual colonies were colourless or only faintly coloured.

Example 3

A suspended mixture of different species of *Candida* was used to inoculate a solid medium in accordance with the invention (essentially corresponding to formulation J as described in Example 1), and incubated at 30° C. for 48 hours. Typical results are shown in FIG. 1, which is a photograph of a plate showing the growth of the inoculum and separate colonies. Even in monochrome, the difference between colonies of different species is apparent.

The invention claimed is:

1. A medium for the detection and/or identification of a *Candida* yeast, the medium comprising: a chromogen; carbohydrate in the range 1-5 gms/liter; and an alcohol, wherein the alcohol includes at least 85 percent by weight ethanol and wherein the medium lacks a hexosaminide activator; the medium being such that growth of the *Candida* yeast under appropriate conditions results in hydrolysis of the chromogen to generate a chromophore of a derived colour which is a different colour from that generated by hydrolysis of the chromogen in a standard medium comprising the same chromogen and carbohydrate, in the same concentrations, but without alcohol.

2. A medium according to claim 1, wherein the chromogen is hydrolysed in the presence of *C. albicans* to give a chromophore with a derived colour.

3. A medium according to claim 1, wherein the carbohydrate is present in an amount in the range 2-4 gms/liter.

4. A medium according to claim 3, wherein the carbohydrate comprises glucose.

5. A medium according to claim 1, wherein the carbohydrate comprises malt extract.

6. A medium according to claim 1, wherein the alcohol is present in an amount in the range 1-10 mls/l.

7. A medium according to claim 6, wherein the alcohol is present in an amount in the range 2-8 mls/l.

8. A medium according to claim 7, wherein the alcohol is present in an amount in the range 5-7 mls/l.

9. A medium according to claim 1, wherein the alcohol comprises ethanol.

10. A medium according to claim 1, wherein the chromogen comprises 5-bromo-4-chloro-3-indolyl N-acetyl β-D-glucosaminide or 5-bromo-6-chloro-3-indolyl phosphate p toluidine salt or 5-bromo-6-chloro-3-indolyl N-acetyl β-D-glucosaminide or X-Gal NAc (wherein Gal is galactose, NAc is an N-acetyl group and X is a chromophore) or 5-bromo-4-chloro-3-indolyl phosphate p toluidine salt or 6-chloro-3-indoxyl-phosphate.

11. A medium according to claim 1, further comprising one or more of the following: malic acid; peptones; and $KH_2PO_4$.

12. A method of detecting and/or identifying a *Candida* yeast in a sample, the method comprising the steps of: contacting the sample with a medium in accordance with claim 1; incubating the medium, under appropriate conditions, to allow growth of the *Candida* yeast; and detecting the presence of a chromophore having a derived colour indicative of the presence of the *Candida* yeast.

13. A method of detecting and/or identifying *C. albicans* in accordance with claim 12.

14. A method according to claim 12, wherein the medium is incubated at a temperature in the range 30-37° C. for no more than 36 hours.

15. A method according to claim 14, wherein the medium is incubated at a temperature in the range 30-35° C. for no more than 24 hours.

16. A method according to claim 15, which distinguishes between *C. albicans, C. tropicalis* and *C. krusei*.

* * * * *